United States Patent [19]

Koenig

[11] Patent Number: 5,027,453

[45] Date of Patent: Jul. 2, 1991

[54] WATER BED SAFETY LINER

[76] Inventor: Kevin C. Koenig, 4900 N. Ocean Blvd. Apt. #1717, Ft. Lauderdale, Fla. 33308

[21] Appl. No.: 560,161

[22] Filed: Jul. 31, 1990

[51] Int. Cl.⁵ .............................................. A47C 27/08
[52] U.S. Cl. ......................................... 5/400; 5/451; 5/452; 5/460
[58] Field of Search .................. 5/400, 451, 452, 460, 5/474, 498

[56] References Cited

U.S. PATENT DOCUMENTS

| | | | |
|---|---|---|---|
| 3,707,735 | 1/1973 | Carson, Jr. ................................. | 5/451 |
| 3,735,432 | 5/1973 | Kreten et al. ......................... | 5/451 X |
| 4,040,133 | 8/1977 | Gilreath ................................. | 5/451 |
| 4,107,799 | 8/1978 | Lambert ............................... | 5/451 X |
| 4,186,455 | 2/1980 | Fox, Jr. et al. ......................... | 5/451 |
| 4,187,566 | 2/1980 | Peterson ................................ | 5/451 |
| 4,352,217 | 10/1982 | O'Rourke ............................. | 5/451 |
| 4,393,531 | 7/1983 | Hodel .................................... | 5/451 |
| 4,506,397 | 3/1985 | Fogel et al. ............................ | 5/451 |
| 4,712,262 | 12/1987 | Viggiano .............................. | 5/498 X |
| 4,713,852 | 12/1987 | Fox, Sr. et al. ....................... | 5/451 |
| 4,745,646 | 5/1988 | Strubel ................................. | 5/451 |

Primary Examiner—Michael F. Trettel
Attorney, Agent, or Firm—Malin, Haley, McHale, DiMaggio & Crosby

[57] ABSTRACT

An improved waterbed safety liner including a water impervious bottom liner sheet integrally joined to a four-sided firm foam perimeter support cushion which itself is wrapped in plastic water impervious sheet forming an entire unit having waterproof integrity to receive the waterbed bladder. The safety liner includes a hose access valve in the bottom of the liner for ease in drainage of the waterbed bladder, a valve stabilizer for improved access to the bladder for filling and emptying the bladder, hinge-like construction of the lateral end peripheral foam support cushions to permit folding of the safety liner for storage and transport and a plurality of sheet grippers for use with conventional contoured bed sheets.

8 Claims, 4 Drawing Sheets

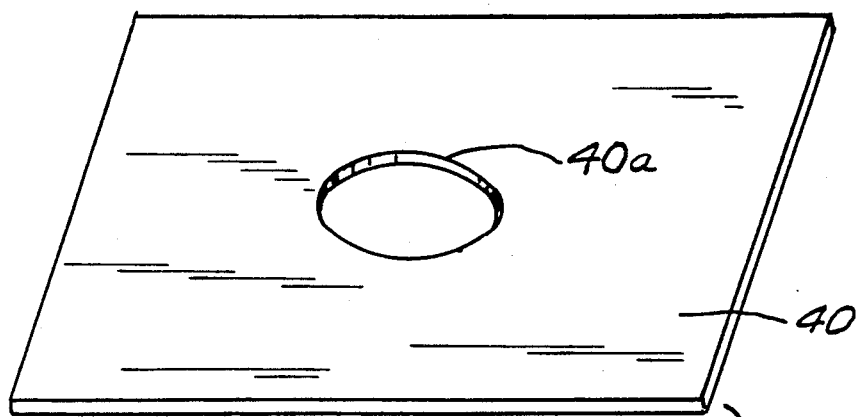
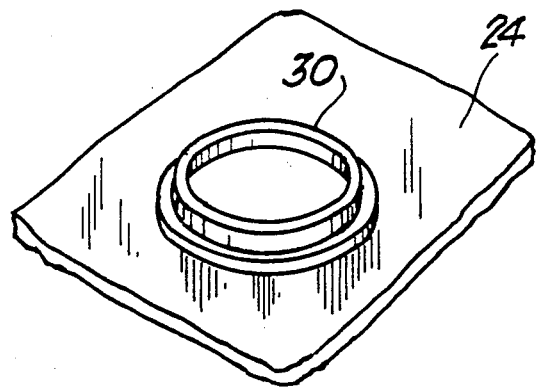
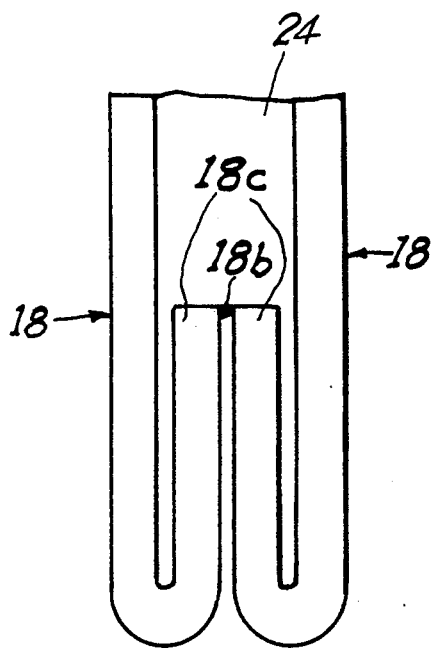
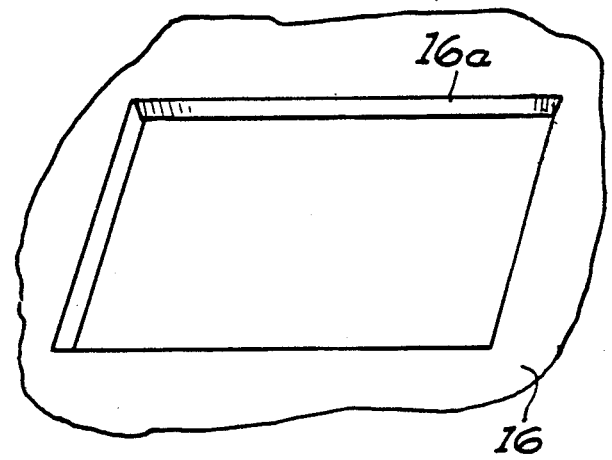
FIG. 9.
FIG. 8.

WATER BED SAFETY LINER

BACKGROUND OF THE INVENTION

1. Field of the Invention

This invention relates generally to an improved water bed safety liner, and specifically to a water bed safety liner that includes a bottom liner integrally joined to a four sided foam perimeter support cushion that itself is wrapped in a plastic sheet to make the entire unit, including the perimeter support cushion, waterproof. The safety liner also includes a valve in the bottom liner for ease in drainage of the waterbed mattress bladder, a valve stabilizer to ensure complete drainage of the bladder, and a plurality of sheet grippers to provide for use with conventional contoured bed sheets. The safety liner includes hinge-like construction at each end allowing the unit to be folded into a compact unit for storage and shipping purposes.

2. Description of the Prior Art

Most conventional water beds include a hardwood frame, a sheet of plastic which is used as a safety liner and a large bladder, filled with water, that acts as the waterbed mattress which is mounted over the safety liner within the hardwood frame. It is desirable to emulate in a waterbed certain characteristics found in traditional bedding (padded spring mattresses and the like) such as sitting comfortably on the side of the bed for entry or egress and using conventional contoured bed sheets. The prior art shows a variety of devices which attempt to create in a waterbed having one or more of the attributes found in padded and spring bedding. One important aspect is the support provided by the perimeter frame around the water filled bladder. U.S. Pat. No. 4,703,531, issued to Bissett, Sept. 3, 1987 and U.S. Pat. No. 4,799,277, issued to Goodale, Jan. 24, 1989 deal with various types of padded peripheral rails. Some waterbed "mattresses" have been called "hybrid" and use a variety of foam rail configurations, an example of which is shown in U.S. Pat. No. 4,745,646, issued to Strobell, May 24, 1988. A reinforced wall, "soft-side" waterbed is shown in U.S. Pat. No. 4,771,491, issued to Fogel et al., Sept. 20, 1988. A waterbed with removable side cushions is shown in U.S. Pat. No. 4,637,082, issued to Moore et al., Jan. 20, 1987. U.S. Pat. No. 4,186,455 issued to Fox, Jr. et al. shows a composite waterbed mattress that uses some foam adjacent the hardwood frame in conjunction with other foam cushions to provide an outer peripheral surface for the mattress which is suitable for sitting. None of the references provide a safety liner that is integrally formed including a comfortable peripheral support for sitting that is also suitable for use with conventional contoured sheets.

Drainage of the bladder in a waterbed is a problem because the elevation of the hardwood frame side edges requires that the hose be brought from the bottom of the mattress up over the sides and then back down again requiring a syphon to completely empty the bladder. With the safety liner in accordance with the present invention, the bladder can be drained by gravity below the bladder support surface without the syphon-effect through the safety liner floor.

The present invention overcomes deficiencies in the prior art by providing a safety liner that includes a plastic sheet floor integrally constructed to a firm yet comfortable foam peripheral core wrapped in a plastic sheet that is supported on the hardwood frame. The foam peripheral support cushion is sized, shaped and positioned such that it is comfortable to sit on, making for easy entry and egress from the waterbed mattress. The safety liner encloses and contains the entire bladder of the waterbed (except the top surface) in a watertight enclosure. The configuration of the foam support cushion can also reduce the amount of hardwood frame required. Other advantages provided by the invention include a foam core cross sectional configuration that greatly aids in the use of conventional contoured sheets, a fold-up construction for storage and shipping, sheet grippers and a strategically located drain valve which permits the mattress bladder to be easily drained when necessary.

It is an object of this invention to provide an improved waterbed safety liner which provides for a soft edge bed having easy entry and egress while safely encompassing the water-filled bladder in a water impervious liner.

It is another object of this invention to provide an improved waterbed safety liner which can be compactly folded for storage and shipping purposes without sacrificing the watertight integrity of the safety liner.

It is another object of this invention to provide an improved waterbed safety liner that includes a drain valve and valve stabilizer for simplified hose draining of the water-filled bladder by gravity without the need for a syphon effect.

Yet still another object of this invention is to provide an improved waterbed safety liner that, through its configuration, allows for the use of conventional contoured sheets in a conventional manner while still incorporating sheet grippers to reduce hammocking effect.

Still another object of the invention is to provide an improved waterbed safety liner that safely contains water should the bladder develop a leak while greatly reducing the cost of construction and the amount of hardwood required for the frame.

In accordance with these and other objects which will be apparent hereinafter, the instant invention will now be described with particular reference to the accompanying drawings.

BRIEF SUMMARY OF THE INVENTION

An improved safety liner for a waterbed for mounting on and within a hardwood waterbed frame, said safety liner comprising a four sided peripherally disposed dense foam core wrapped in a water impervious plastic sheet that is integrally connected to a bottom floor liner for encompassing the mattress bladder. The dense foam core is configured in cross section such as to rest upon and interlock with the entire four sided hardwood waterbed frame members forming a soft edge or soft sided support cushion on all four sides of the waterbed frame.

In cross sectional shape, the dense foam core support cushion forming the peripheral support that is mounted on the wooden frame includes a first upper section substantially rectangular in shape slightly larger in width than the hardwood frame and sized in width and height to fit across the top surface and downwardly flush against the top and inside surfaces of the hardwood frame member, forming an L-shaped interlock with the hardwood frame members on all four sides of the bed. Thus, conventional contoured sheets can be used and fitted over the foam support cushion outer and lower surfaces for disposition between the upper surface of the hardwood frame and the inside and the outer lower peripheral surface of the support cushion.

Since the bottom floor liner and the contiguous sheet that wraps the foam support cushion are sealably attached as one integrated unit (either through heat sealing or adhesive), the liner wrapped four sided cushion act as an integral unit to safely encompass and contain any water leakage from the mattress bladder.

In one embodiment the safety liner can be constructed so that the entire unit can be folded into very compactly, useful for storage and shipping purposes. In this embodiment lateral end members of the liner including the end foam support cushions include a centerline break in which the sections of the end foam support cushions are covered with the water impervious plastic sheet and the outside wall is sealed together forming a movable hinge in the center of each end which allows the segments at each end to be folded inwardly. Excess liner is wrapped around the foam support cushions so that its folded support cushions are aligned in parallel allowing the end segments and the side members to be flushly packed together. The plastic hinge, which may be formed by a heat sealed piece along the outside wall at each lateral end face, still preserves the watertight integrity of the entire safety liner. Furthermore, at the mitered, rounded corners of the safety liner, there is enough stretch or give to permit such folding to take place. This hinge feature that permits break down greatly reduces shipping costs and the storage room required without sacrificing the watertight integrity of the entire safety liner.

The cross sectional configuration of the safety support cushion further enhances the use of straps having sheet gripping clamps which can be disposed between the interlock of the hardwood frame and the surface of the support cushion at strategic locations on all sides of the bed. The gripper straps and sheet gripper clamps provide structural flexibility to the bed sheets when the filled bladder is compressed reducing the hammocking effect on the bed sheets.

The safety liner includes an access valve (such as a "Roberts" valve) disposed through the bottom liner for use with an aperture in the plywood frame that supports the water bladder to allow for access of a drain hose for draining the bladder conveniently and quickly, eliminating the need to produce a syphon or pump to drain the bladder. In addition to the access valve in the liner bottom, a valve stabilizer is included, which is a thickened sheet of plastic or cardboard which is used to cover the hose access valve in the bottom of the liner. This enlarged support sheet allows for a much larger hole to be cut through the plywood frame beneath the liner valve which thus permits the liner valve and the bladder valve to be pulled through the plywood frame hole and thus positioned below the underside of the plywood frame for completely draining the mattress bladder by gravity. The valve stabilizer enhances the horizontal support over the enlarged opening in the plywood frame so that when the bladder is filled, the area beneath the bladder valve and liner valve will not allow the filled bladder to be depressed through the larger opening in the plywood. The plastic valve stabilizer can be removed when necessary to position the drain or fill hose.

The safety liner, in accordance with the present invention, is thus constructed of a plastic water-impervious sheet forming a bottom liner which is sealably joined on all four sides to a substantially dense foam core having an inverted L-shaped cross section which is sealed by a plastic sheet affixed to the bottom liner. The dense foam provides a comfortable cushion adjoining the bladder in a common plane making the bladder and cushion comparable to a conventional spring and padded mattress while reducing the amount of hardwood frame necessary because of the elevated and interlocking configuration of the foam over the frame. By overlapping the hardwood frame and extending the dense foam core from the thick plywood floor support and the inside edge of the hardwood frame members upwardly to the top the hardwood frame, the frame member cross sectional size is reduced, greatly reducing the expense of materials.

In accordance with these and other objects which will be apparent hereinafter, the instant invention will now be described with particular reference to the accompanying drawings.

BRIEF DESCRIPTION OF THE DRAWINGS

FIG. 8 shows a top plan view partially cut away of the safety liner in a folded position.

FIG. 9 shows an exploded partially cut away view of the plywood support floor, the liner valve, and the valve stabilizer.

PREFERRED EMBODIMENT OF THE INVENTION

Figure 1:
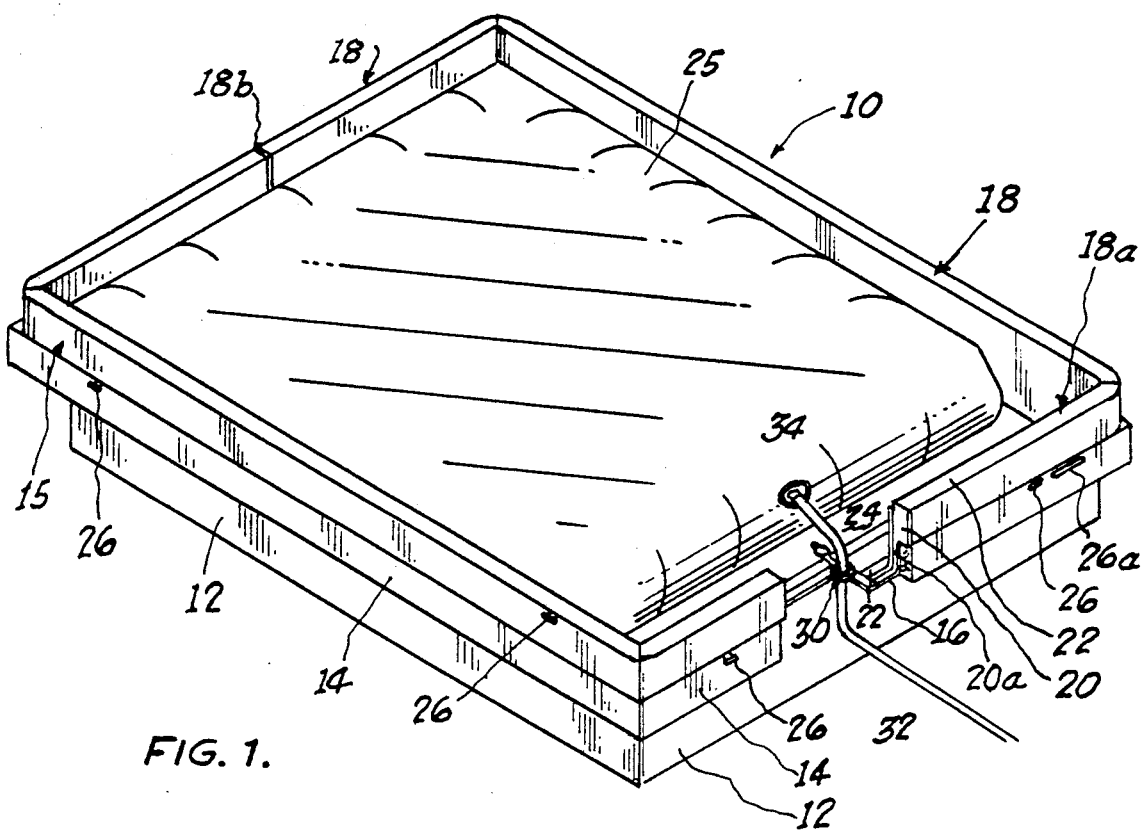
FIG. 1 shows a perspective view partially cut away of the present invention.

Referring now to the drawings, the present invention is shown generally at 10 comprised of an improved safety liner for use with a water-filled bladder 28 which acts as the waterbed mattress supported on a rigid planar plywood surface 16 all of which is mounted on a base hardwood frame 12. The hardwood frame is rectangular in shape and defines the base support for the entire waterbed.

A secondary upper hardwood frame is comprised of frame members 14 attached to the rigid planar surface 16 defining the perimeter of the waterbed.

The safety liner 10 in accordance with the present invention includes a four-sided peripheral support cushion 18 mounted on and within upper frame 14. The cushion 18 is constructed of a dense foam core 20 somewhat in an inverted L-shape cross section sealably wrapped completely in a water impervious plastic sheet 22, all of which is attached either by adhesive or heat welding to the bottom water impervious plastic sheet 24. The support cushion 18 extends around the entire perimeter of the bed with a substantial portion of the cushion resting upon the hardwood frame members 14, with an additional portion of foam 20a extending downwardly, parallel to and contacting the inside surface of all frame members 14 terminating in contact with the rigid planar surface 16. The effect of this interlocking action between the peripheral hardwood frame members 14 and the foam support cushion 18 are explained in greater detail below. The water-filled bladder 28 includes a valve 34 which is used to fill and empty the bladder 28. In accordance with the present invention the rigid planar surface 16 which acts to support bladder 28 includes an aperture positioned to align itself with a Robert's valve 30 in bottom liner 24 which permits a hose 32 to be attached up through the supporting planar surface 16 so that the bladder 28 can be conveniently drained by gravity through valve 34 with hose 32 disposed through the valve 30 with the valve cap open as shown. A valve stabilizer (not shown in FIGS. 1 and 2) may be employed and is discussed in greater detail below.

Figure 2:
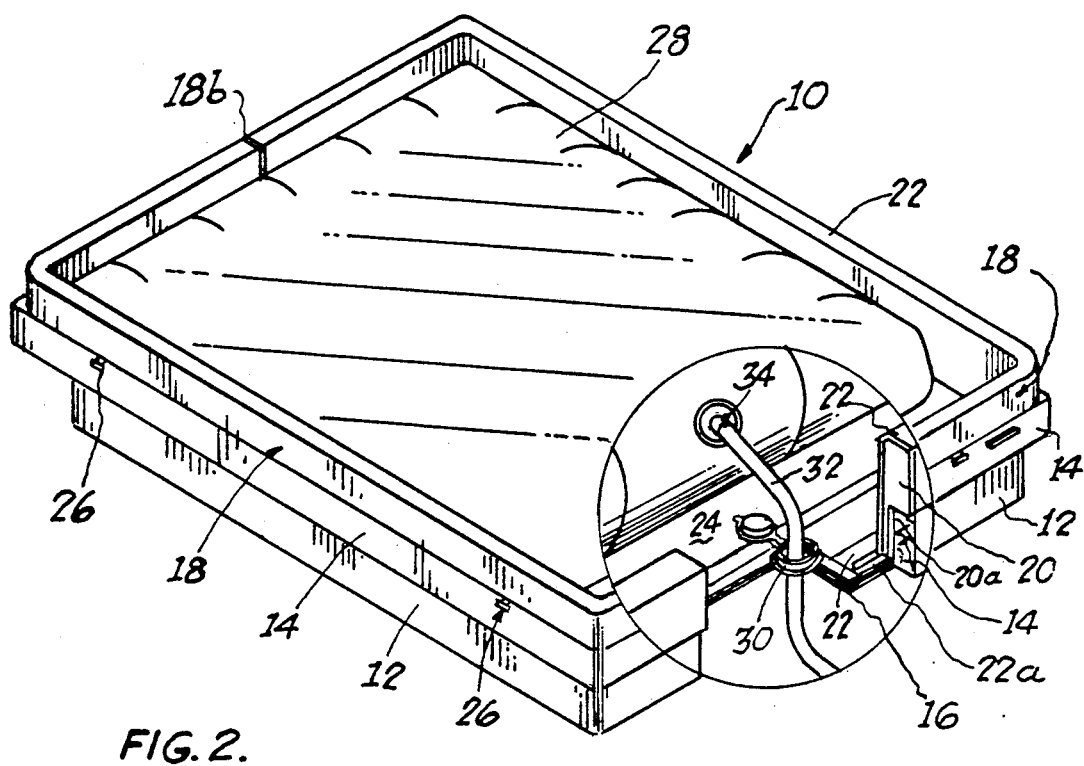
FIG. 2 shows a perspective view of a safety liner in accordance with the present invention with an enlarged cut away view.

As shown in FIG. 2, the support cushion 18 includes the dense foam core 20 which is shaped to include an elongated portion 20a which resides vertically along the inside surface of frame member 14. Thus the bladder 28 contacts and is contained by the foam support cushion about its periphery. The support cushion configuration allows the height of all of the hardwood frame members 14 to be reduced thereby reducing the amount of wood necessary for the support frame 14. Also note in FIG. 2 that the plastic sheet 22 is stretched completely around the foam core 20 and doubled back upon itself as shown in area 22a forming a watertight seal around the foam core 20 and around the entire periphery of the waterbed bottom liner 24. Further, the plastic sheet 22 is itself affixed by heat welding to the bottom plastic sheet 24 forming the bottom liner of the safety liner thus forming a completely integral plastic safety liner that can contain any water that should leak from the bladder 28. This includes the corners of the support cushion which are all integrally joined together. A hinge 18b at each end of the safety liner permits folding of the safety liner, discussed below in greater detail.

The area around the access valve 30 is also heat sealed so that when the cap of the valve 30 is closed, the entire safety liner will contain any water should the bladder leak. Note also in FIG. 2 that through the location of valve 30 permitting a drain hose 32 to be attached to the valve 34 in bladder 28, the bladder 28 can be completely emptied because of the location of valve 30 and the fact that the hose does not have to go from a low point inside the safety liner up over the side rails requiring a syphon. A valve stabilizer may also be used and is discussed with respect to FIG. 9.

Disposed also between the support cushion 18 and the hardwood frame members 14 at strategic locations (typically two per side) are sheet gripping clamps 26 which interlock with a sheet gripping member 26a to provide some resilient movement of the bed sheet (not shown) so that a hammocking effect is not created with the use of conventional contoured sheets if large weight compress the bladder 28. Because of the L-shaped interlock of the support cushion 18 and the hardwood frame members 14, conventional contoured sheets can be employed quite readily. The overlap on the contoured sheets fits over the outside surface of cushion 18 and between the cushion and the frame member 14 surfaces in an interlocking fashion, much like with a conventional mattress. There is enough flexibility in the dense foam core 20 due to the configuration and thickness of the extended cushion portion 20a that permits some manual movement of the upper cushion edge away from the inside surface of hardwood frame members 14 on all sides to allow a person to quickly install or remove the bed sheets.

Figure 3:
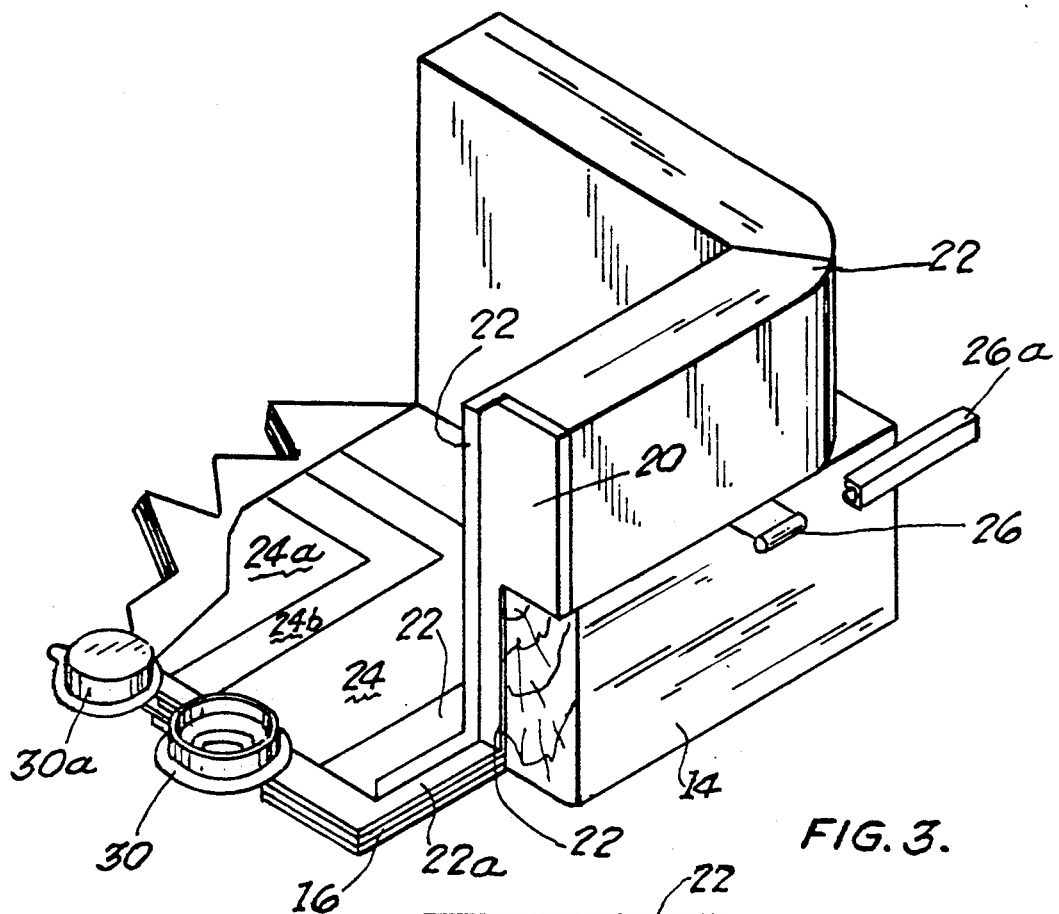
FIG. 3 shows a perspective view partially cut away of a segment of the present invention.

FIG. 3 shows the plastic sheet 22 (which may be PVC or vinyl) wrapped completely around the dense foam core 20 and overlappingly attached on itself in area 22a and further heat welded to the plastic bottom liner sheet 24 which may include multiple layers 24b and 24a forming a trimilitate liner bottom. Note that due to wrapping the dense foam core 20, no water will contact the foam core 20 and the entire safety liner, including the support cushion 18, form one four-sided waterproof integral unit. Secondly, the plastic sheet 22 wrapped around the foam 20 acts to form an interlock through its engagement with the inside and upper surfaces of the wooden frame member 14 further allowing conventional contour sheets to be interlocking between the surfaces and holding them together.

The rigid planar supporting surface 16 may be of a suitable thick plywood which has an aperture aligned with the hose access valve 30 (shown in the open position) which includes an attachable, sealable cap 30a. The size of the plywood opening may be enlarged with the use of a valve stabilizer, discussed below.

The sheet gripper clamp member 26a is an elongated member having a cylindrical hollow interior with a slot running its length along one side to permit engagement with the cylindrically shaped end of the sheet gripper clamp 26 by coaxial positioning with bed sheet material trapped about the sheet gripper clamp 26, firmly holding the bed sheet in place. In the view shown in FIG. 3, the clamp 26 is shown extended out of its normal position which would be flush with the edge of the frame member 14 and cushion 18 outer surface.

Figure 4:
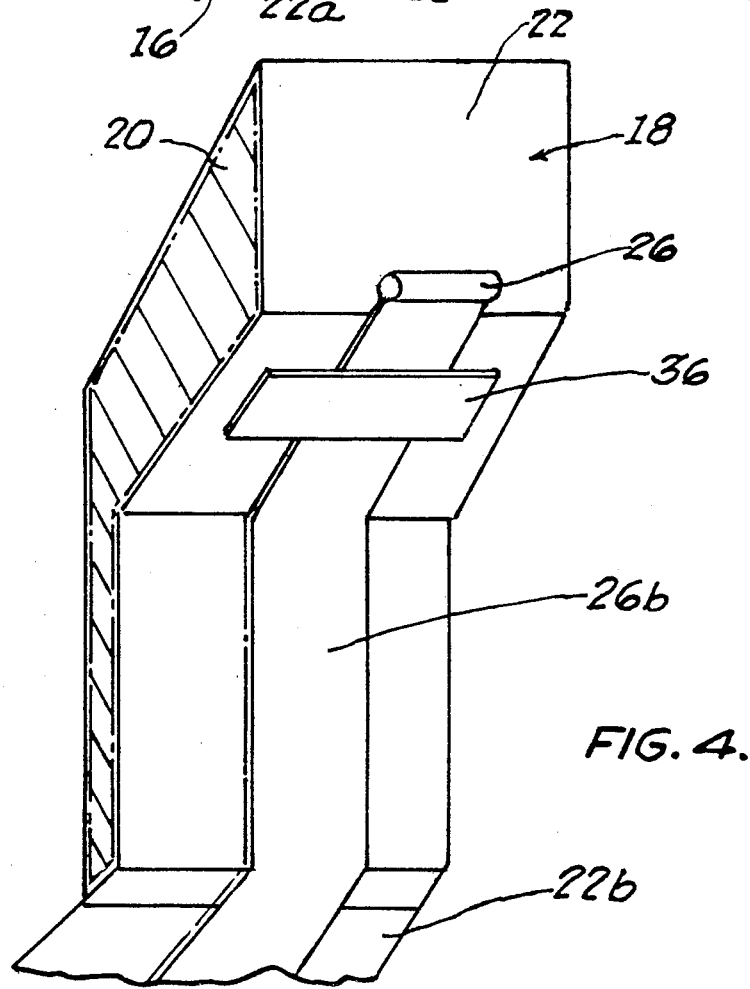
FIG. 4 shows a perspective view partially cut away of the sheet gripper strap and sheet gripper utilized in the present invention.

FIG. 4 shows the sheet gripper strap 26b affixed to the bottom liner 22b by heat welding and includes a positioning strap 36 mounted on the exterior wall of the cushion 18 for positioning the sheet gripper clamp 26 in the proper location. The use of the sheet gripper strap and clamp provide flexibility when the water mattress is compressed to reduce the hammocking effect caused from tension in the bed sheets.

Figure 5:
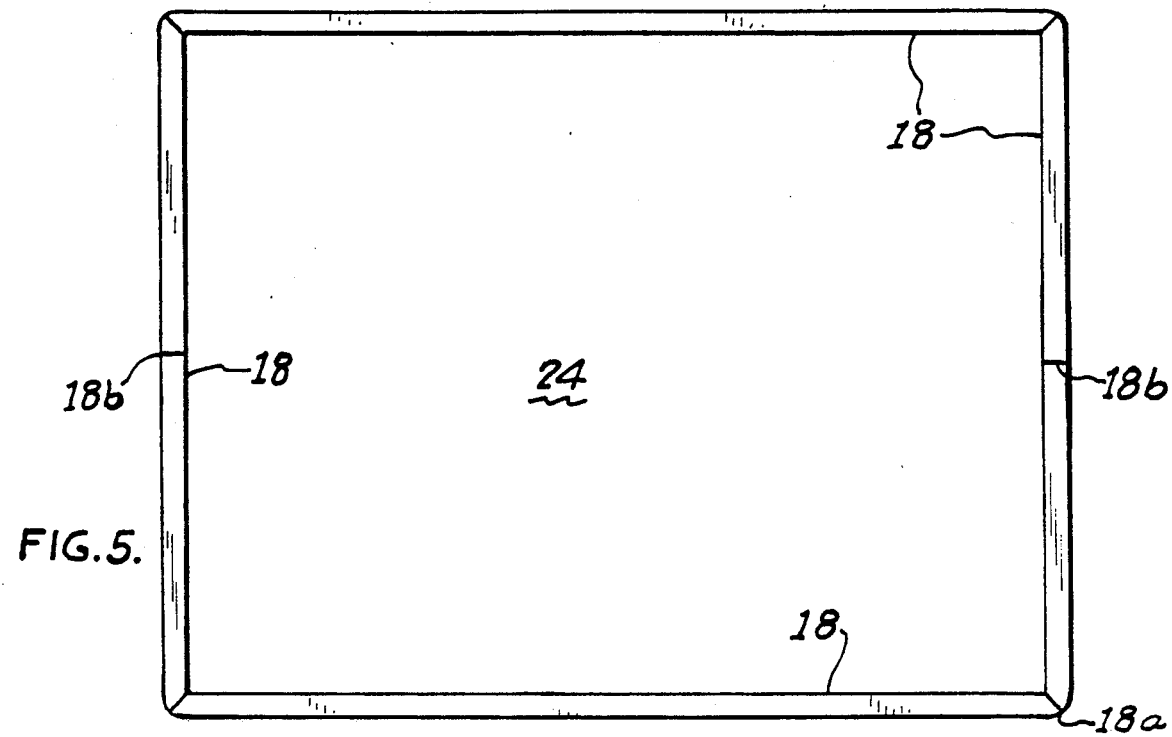
FIG. 5 shows a side elevational view of the present invention.
Figure 6:
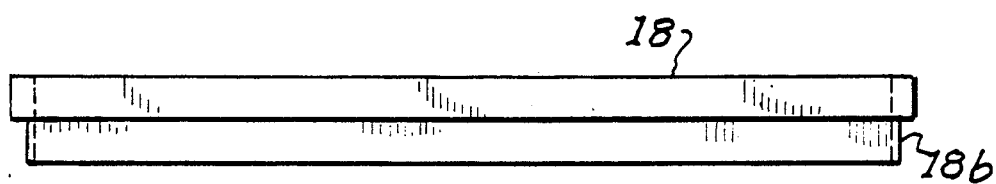
FIG. 6 shows a top plan view of the present invention.

FIGS. 5 and 6 show the overall configuration of the safety liner in accordance with the present invention which includes the bottom plastic sheet 24 which is joined continuously around the bottom liner periphery to the foam cover 22 so that the support cushion 18 and the bottom liner 24 form an integral watertight unit about the hardwood frame 14.

Figure 7:
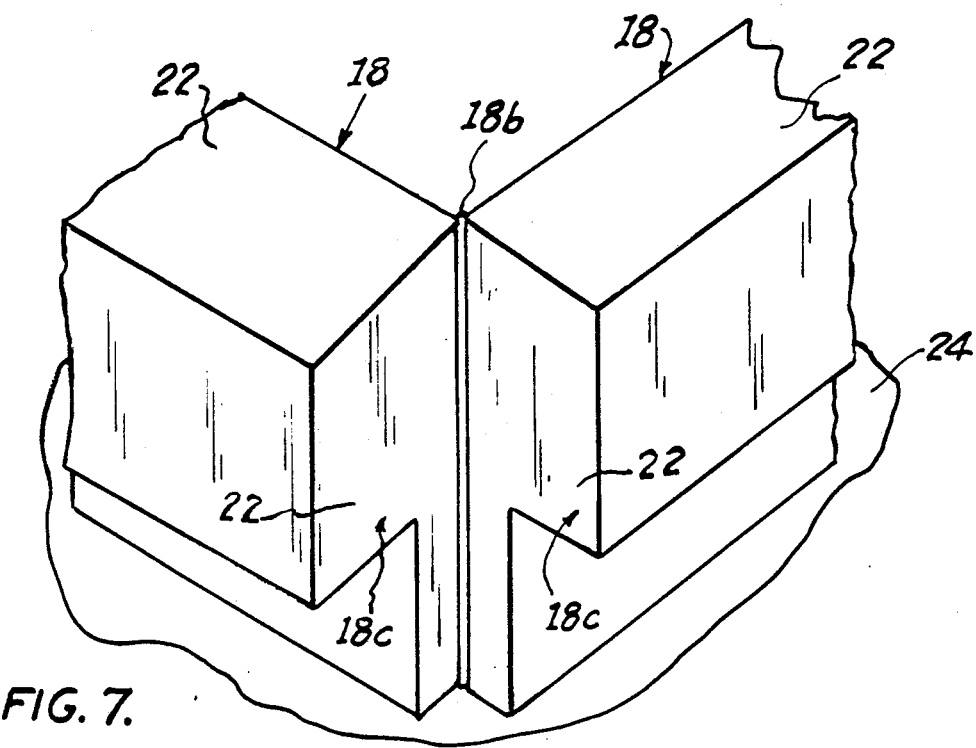
FIG. 7 shows a cut away perspective view of the hinge used at the end segments of the safety liner that permit folding of the safety liner.

Referring now to FIGS. 7 and 8, the hinge 18b is shown disposed at the middle of the foam cushion supports at each lateral end of the safety liner. The purpose of hinge 18b is to allow the lateral end segments to be collapsed inwardly in order to fold the entire safety liner into a compact unit as shown in FIG. 8. The end face segments 18c of the support cushions 18 are covered with the water impervious plastic sheet so that none of the inside foam is exposed. When the safety liner is installed in the bed frame, the end faces 18c of the lateral segments are flush and are compressed together, and along with the outside heat sealed hinge 18b, provide a watertight interior environment in the liner. There is sufficient flex or give in the end corners of the safety liner to permit collapsing the safety liner as shown in FIG. 8 reducing its overall size to be conveniently packed away or shipped from the factory, greatly reducing shipping costs.

Referring now to FIG. 9, the access valve 30 may include a valve stabilizer 40 having an access aperture 40a that is disposed over the area surrounding valve 30 in the liner bottom 24. In this embodiment the plywood floor 16 may include an enlarged opening 16a which greatly exceeds the size of the access valve diameter 30. The enlarged opening 16a permits the liner 24 and access valve 30 and the bladder valve (not shown in FIG. 9) to be pulled through opening 16a, below the level of the plywood support floor 16 so that all the water in the bladder will drain out by gravity when necessary. The valve stabilizer 40 is made of a thickened sheet of plastic or cardboard-like material to provide some rigidity which will support the bladder and liner 24 over opening 16a so that the bladder (when filled with water) will not sag or be forced through opening 16a. During the mattress filling operation, the stabilizer 40 can remain in place when the hose is positioned through valve 30 and aperture 40a in valve stabilizer 40 into the bladder valve.

In summary, the waterbed safety liner as described in the present invention provides a comfortable entry and exit to and from the waterbed mattress to emulate a soft sided bed effect, safely contains the entire water bladder, can be folded for shipping and storage, greatly reduces construction costs of both the safety liner and the hardwood frame, and permits the use of regular contour sheets. The safety liner, due to its configuration, further includes a bottom drain valve for gravity drain eliminating the need for a syphon or pump. Finally, the improved safety liner includes sheet gripping clamps with straps that give the necessary flexibility to the bed sheets to reduce the hammocking effect when the waterbed bladder is compressed.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An improved waterbed safety liner for use with a hardwood frame which provides a soft edge bed comprising:
   a four sided dense foam pad formed in the shape of a rectangle configured to fit upon and within a hardwood waterbed frame, said pad including an upper portion and a lower portion of reduced width forming substantially in cross section an inside L-shaped corner that fits peripherally about the top and inside of each hardwood frame member;
   a first water impervious sheet wrapped about said foam pad in a water impervious sealed connection;
   a second water impervious sheet connecting continuously to the first sheet forming a bottom liner; and
   outlet valve means disposed in said bottom liner portion to permit access of a hose through said liner.

2. A waterbed safety liner as in claim 1, in combination with a hardwood frame including:
   a waterbed rigid support platform having an aperture therein, said aperture positioned to be aligned with the outlet valve means in said waterbed safety liner, said support platform aperture being substantially larger than the size of the outlet valve means in said safety liner,
   a valve stabilizer means disposed about said and on top of said safety liner surrounding said outlet valve means to provide additional horizontal support over said support platform aperture.

3. An improved waterbed safety liner for use with a hardwood frame which provides a soft edge bed comprising:
   a four sided dense foam pad formed in the shape of a rectangle configured to fit upon and within a hardwood waterbed frame, said pad including an upper portion and a lower portion of reduced width forming substantially in cross section an inside L-shaped corner that fits peripherally about the top and inside of each hardwood frame member;
   a first water impervious sheet wrapped about said foam pad in a water impervious sealed connection;
   a second water impervious sheet connecting continuously to the first sheet forming a bottom liner;
   bed sheet clamping means; and
   a plurality of straps affixed to said bottom liner, said straps being elongated to project along the outside lower edge of said foam pad, said bed sheet clamping means attached to said strap ends for attachment to a sheet gripping means.

4. An improved waterbed safety liner for use with a hardwood frame which provides a soft edge bed comprising:
   a four sided dense foam pad formed in the shape of a rectangle configured to fit upon and within a hardwood water frame, said pad including an upper portion and a lower portion of reduced width forming substantially in cross section and inside L-shaped corner that fits peripherally about the top and inside of each hardwood frame member; and
   a first water impervious sheet wrapped about said foam pad in a water impervious sealed connection; and
   a second water impervious sheet connecting continuously to the first sheet forming a bottom liner;
   said four-sided dense foam pad having first and second lateral ends each having lateral end segments and first and second longitudinal sides joined together to form said rectangle, said first and second lateral ends each including a hinge substantially in the center of each lateral end, each hinge forming a sealed watertight joint between end segments along the outside edges of said end segments thereby permitting the entire safety liner to be folded at the hinge joints for storage and shipping.

5. A safety liner for a waterbed, said waterbed having a rigid rectangular frame, said rectangular frame having substantially peripheral support members having a rectangular cross section, said peripherally disposed cross members including a top surface, an outside surface facing away from the waterbed, and an inside surface, said safety liner comprising:
   a cushion for supporting a person disposed on the top surface of said peripheral waterbed support members, said cushion including a vertical surface disposed flush with the inside surface of said peripheral frame members, said cushion disposed completely around and supported on said peripheral waterbed frame members;
   a water impervious sheet wrapped around and forming the outside surface of said cushion forming a water impervious barrier about the entire cushion disposed about the peripheral frame members;
   a second water impervious sheet connected about its perimeter to said first sheet forming an interior water impervious liner between all the inside edges of said cushion whereby a waterbed bladder may be safely disposed within said peripheral cushion in a watertight environment;

said second sheet forming said interior liner including an aperture for receiving a hose or conduit for filling or draining said waterbed bladder; and means for sealing said hose receiving aperture to form a watertight seal about said aperture.

6. A waterbed safety liner as in claim 5, said waterbed rigid frame including a rigid planar horizontally supported surface for receiving said second sheet of said safety liner and said waterbed bladder mattress, said rigid planar horizontally supported surface including an enlarged aperture substantially larger than said sheet hose receiving aperture, said planar surface aperture sized to have the sheet hose receiving aperture and said bladder valve through said aperture to permit draining said bladder by gravity when desired; and a planar support sheet for providing horizontal support sized to cover said rigid planar aperture for providing support over said safety liner hose receiving aperture for said bladder.

7. A safety liner for a waterbed, said waterbed having a rigid rectangular frame, said rectangular frame having substantially peripheral support members having a rectangular cross section, said peripherally disposed cross members including a top surface, an outside surface facing away from the waterbed, and an inside surface, said safety liner comprising:

a cushion for supporting a person disposed on the top surface of said peripheral waterbed support members, said cushion including a vertical surface disposed flush with the inside surface of said peripheral frame members, said cushion disposed completely around and supported on said peripheral waterbed frame members;

a water impervious sheet wrapped around and forming the outside surface of said cushion forming a water impervious barrier about the entire cushion disposed about the peripheral frame members;

a second water impervious sheet connected about its perimeter to said first sheet forming an interior water impervious liner between all the inside edges of said cushion whereby a waterbed bladder may be safely disposed within said peripheral cushion in a watertight environment;

a plurality of elongated straps connected to said second sheet and a portion of said first sheet disposed about said cushion, each of said straps being positioned outwardly from the inside of the liner for engaging the inside and top surfaces of said rigid member, said strap and cushion surface including strap retaining means, and means attached to the end of said strap for affixing a sheet to the end of said strap.

8. A safety liner for a waterbed, said waterbed having a rigid rectangular frame, said rectangular frame having substantially peripheral support members having a rectangular cross section, said peripherally disposed cross members including a top surface, an outside surface facing away from the waterbed, and an inside surface, said safety liner comprising:

a cushion for supporting a person disposed on the top surface of said peripheral waterbed support members, said cushion including a vertical surface disposed flush with the inside surface of said peripheral frame members, said cushion disposed completely around and supported on said peripheral waterbed frame members;

a water impervious sheet wrapped around and forming the outside surface of said cushion forming a water impervious barrier about the entire cushion disposed about the peripheral frame members;

a second water impervious sheet connected about its perimeter to said first sheet forming an interior water impervious liner between all the inside edges of said cushion whereby a waterbed bladder may be safely disposed within said peripheral cushion in a watertight environment;

said support cushion having first and second longitudinally disposed side members and third and fourth laterally disposed end members, said third end member including first and second segments divided at substantially the center of said third end member, said first end segment and said second end segment being covered by said first water impervious sheet at each end and a water impervious hinge joining said first and second segments along the outside wall of said cushion forming a watertight barrier, said fourth lateral end having first and second segments divided substantially at the center of said fourth lateral end, said first and second fourth lateral end segments having end faces sealed by said water impervious sheet surrounding said cushion, said first and second fourth lateral end segments joined together by a water impervious hinge forming a water impervious barrier along the outside wall of said fourth lateral support cushion relative to said interior liner bottom wherein said entire safety liner can be collapsed by movement of said third and fourth lateral end first and second segments to allow the safety liner to be stored in a small area or shipped.

* * * * *